(12) United States Patent
Menne et al.

(10) Patent No.: US 6,733,664 B2
(45) Date of Patent: May 11, 2004

(54) FILTRATION DEVICE FOR SEPARATION OF CONCRETIONS, FRAGMENTS OR OTHER BODY MATERIAL FROM LIQUIDS

(75) Inventors: Andreas Menne, Meersburg (DE); Wolfgang Merkle, Meersburg (DE)

(73) Assignee: Ferton Holding S.A., Delemont (CH)

( * ) Notice: Subject to any disclaimer, the term of this patent is extended or adjusted under 35 U.S.C. 154(b) by 40 days.

(21) Appl. No.: 09/946,568

(22) Filed: Sep. 5, 2001

(65) Prior Publication Data

US 2003/0042187 A1 Mar. 6, 2003

(51) Int. Cl.⁷ .............................................. B01D 35/34
(52) U.S. Cl. ....................... 210/110; 210/117; 210/136; 210/311; 210/438; 210/440; 210/445; 210/451
(58) Field of Search ................................ 210/636, 311, 210/438, 440, 443, 445, 451, 110, 117, 416.1, 295, 299, 444; 604/319, 320, 405, 406; 433/91, 92; 55/DIG. 3

(56) References Cited

U.S. PATENT DOCUMENTS

| | | | | |
|---|---|---|---|---|
| 3,482,313 A | * | 12/1969 | Stram | ............................. 433/92 |
| 4,385,891 A | * | 5/1983 | Ligotti | ........................... 433/92 |
| 4,655,754 A | * | 4/1987 | Richmond et al. | ............ 604/323 |
| 5,741,134 A | * | 4/1998 | Davis | ........................... 433/91 |
| 5,876,384 A | * | 3/1999 | Dragan et al. | ............... 604/264 |

OTHER PUBLICATIONS

Pamphlet: Swiss Lithoclast Master, All–in–One Lithotripter by EMS, 10 pages, Germany and Swizterland, date unknown.

* cited by examiner

Primary Examiner—Matthew O. Savage
(74) Attorney, Agent, or Firm—Collard & Roe, P.C.

(57) ABSTRACT

A filtration device for separating concrements, fragments or other body material from liquids which are processed by means of a lithotripter connected to a suction device equipped with a peristaltic valve and sucked out of body cavities. The device has a functional zone having an inlet zone connected at one end to the lithotripter, and an outlet zone connected to the suction device. There is a collection zone mounted on the functional zone and connected to the other end of the inlet zone. A filter element is disposed between the functional zone and the collection zone, so that body material processed by the lithotripter will be deposited in the collection zone, and the filter element will separate the body fluids collected by the lithotripter from the body material.

7 Claims, 2 Drawing Sheets

FILTRATION DEVICE FOR SEPARATION OF CONCRETIONS, FRAGMENTS OR OTHER BODY MATERIAL FROM LIQUIDS

BACKGROUND OF THE INVENTION

1. Field of the Invention

The invention relates to a filtration device for separation of concrements, fragments or other body material from liquids, which are processed by means of a lithotriptor, for example, and by means of a suction device are sucked out of body cavities via a suction line.

2. Prior Art

From the prior art, filtration devices are known. They are used to suck into a vessel calculi or fragments of calculi present in body cavities or other body material that must be removed. These fragments are collected outside the body and sent for subsequent examination.

To remove body calculi from body cavities, however, it is necessary to reduce the size of the calculi, especially those which cannot be removed via a natural duct. This reduction in the size of body calculi is undertaken by mechanical compressive and tensile stresses, which in the case of intracorporeal lithotripsy, are applied to the body calculi with the distal end of a lithotripter functioning as a wave guide. In this process, stresses are generated that cause splitting of fragments from the surface of the calculus. The fragments are then deposited in the body cavity.

Some lithotripsy instruments are additionally provided with a suction device on their working parts. This suction device has at its proximal end, a flexible suction tube extending to a suction device, which preferably is disposed in the vicinity of the lithotripsy instrument. The sucked-out liquid is passed together with the calculus fragments through a vessel. In the vessel, the liquid is separated from the fragments by natural sedimentation.

In a particular embodiment of a lithotripsy instrument, a pinch valve is used to control the suction air, the suction line being routed through the pinch valve. The suction function of the suction device can be appropriately controlled, preferably by a foot-pedal control system. Unfortunately, it has been found that, because of the flow of concrements, fragments, calculus debris or other body materials through the suction line, these materials are deposited at the constriction of the suction line formed by the pinch valve. As a result, it becomes impossible to bring the inside walls of the suction line into complete contact with one another in the region of the pinch valve. Therefore, the suction function cannot be properly stopped at any time, or the suction effect is displaced.

A further major disadvantage of the suction device already known from the prior art is that the fragments must be strained manually out of the suction bottles. This is extremely unhygienic and may well falsify the laboratory result. In addition, it is extremely time-consuming, and there is the risk that part of the calculus fragments may be lost.

Certainly so-called roller pumps are known from the prior art. These are provided with a collection vessel, which usually comprises a glass bottle with a capacity of one liter. One disadvantage in this case is the volume, which inevitably makes it more difficult to manipulate the instrument and thus also the suction device. Another is that straining of fragments is also necessary here.

SUMMARY OF THE INVENTION

The invention is an improvement over the prior art by preventing potential blockages of the suction line by fragments or other body materials in flow direction upstream from the pinch valve, to ensure that the suction control system can be shut off in a properly functioning manner at any time.

The invention provides a filtration device subdivided into a collection zone and a functional zone, wherein the functional zone can be mounted on the collection zone. The functional zone is divided into an inlet and an outlet zone, wherein the outlet zone is additionally provided with a filter element, and that the filtration device is disposed between a one end of a suck-lithotripter and the peristaltic valve.

One of the main advantages of the invention is that, because the filtration device is already disposed upstream from the valve, the pinch function of the valve remains unaffected and so the function is preserved over the useful life of the instrument, regardless of the number and size of fragments.

The filtration device itself is equipped with a flexible supply tube and a flexible discharge tube. The flexible tube on the supply side has a very long suction line and its inside diameter is adapted to the size of the hand piece to be guided in order to perform a lithotripsy treatment. The flexible supply tube has an inside surface with very little roughness, in order to prevent adhesion of concrements, fragments or other body materials. On the discharge side, there is provided a specially designed flexible tube, whose inside diameter, wall thickness and Shore hardness are adapted for operation with the pinch valve.

Thus, a very flexible and soft tube can be used for a simple manipulation of the hand piece and also on its adaptability, while at the same time, a piece of flexible tube consistent with the functions of the pinch valve can be used on the discharge side.

Preferably, the two flexible tubes have different diameters, to ensure that any mix-up of the two flexible tubes during the attachment process will easily be recognized.

The filtration device itself is constructed in two parts. It has a collection zone and a functional zone. The collection zone preferably has a vessel and the functional zone has a cover with appropriate functional elements. The functional elements include a connecting element for the incoming flexible tube, and a connecting element for the outgoing flexible tube, as well as a filter device, which is preferably mounted in the region of the flexible discharge tube. The connecting element for the incoming flexible tube extends into the collection zone of the filtration device, so that concrements, fragments or other body materials present together with liquid in the collection zone as a result of the suction process are retained by the strainer, while the liquid is delivered through the flexible discharge tube in the direction of the suction pump.

The filtration device itself is made of plastic, and so it can be used as a sterile, disposable article. For this purpose the filtration device will be placed in an appropriate sterile package.

To ensure that fragments or other body material cannot be lost during transfer by pouring into another vessel or similar operation, the functional zone is separated from the collection zone, and the collection zone is closed by means of a transportation cover.

In this way, a faulty analysis of the calculi due to ingress of extraneous germs, as is unavoidable in the case of reusable vessels, is prevented by using a sterile disposable product. The flexible tubes can also be made disposable and provided pre-assembled on the filtration unit. To ensure that the suction pump cannot be operated incorrectly due to lack of attention, whereby a pressurization process instead of a suction process may be initiated, a lift check valve must be disposed in the outgoing flexible tube. Thereby damage caused by lack of attention or mistake on the part of the patient can be prevented.

Other objects and features of the present invention will become apparent from the following detailed description considered in connection with the accompanying drawing which discloses two embodiments of the present invention. It should be understood, however, that the drawing is designed for the purpose of illustration only and not as a definition of the limits of the invention.

BRIEF DESCRIPTION OF THE DRAWINGS

In the drawings, wherein similar reference characters denote similar elements throughout the several views.

DETAILED DESCRIPTION OF THE PREFERRED EMBODIMENT

Figure 1:
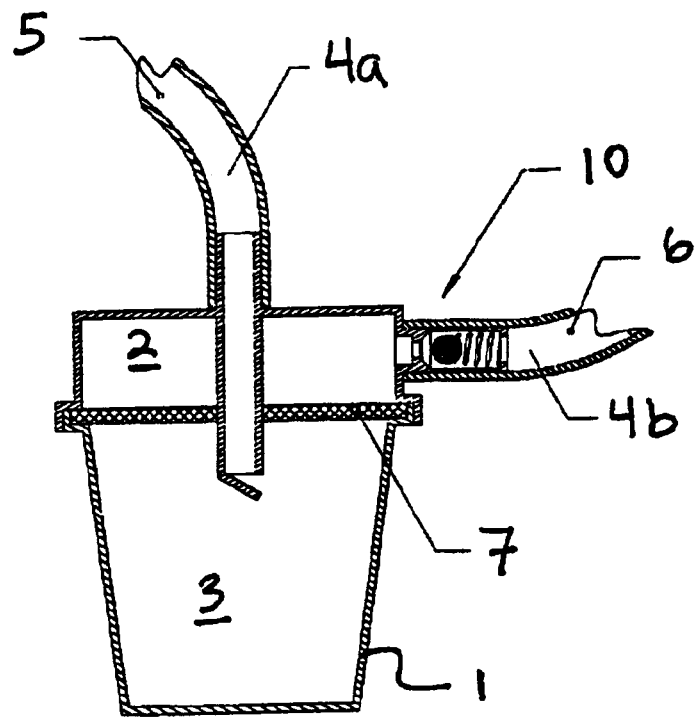
FIG. 1 shows a schematic diagram of the inventive filtration device.

Referring to FIG. 1, there is shown the inventive filtration device 1 which includes a container 1a and a cover 16 having a functional zone 2 and a collection zone 3.

Figure 2:
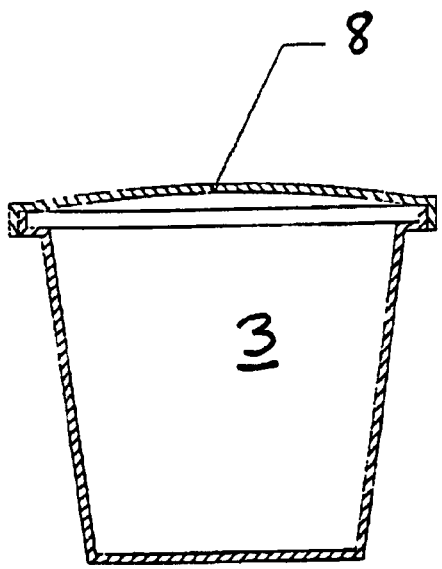
FIG. 2 shows a schematic diagram of one possible use of the filtration device together with a transportation cover; and, FIG. 3 shows a schematic diagram of the principle of operation of the filter device together with a pinch valve.
Figure 3:
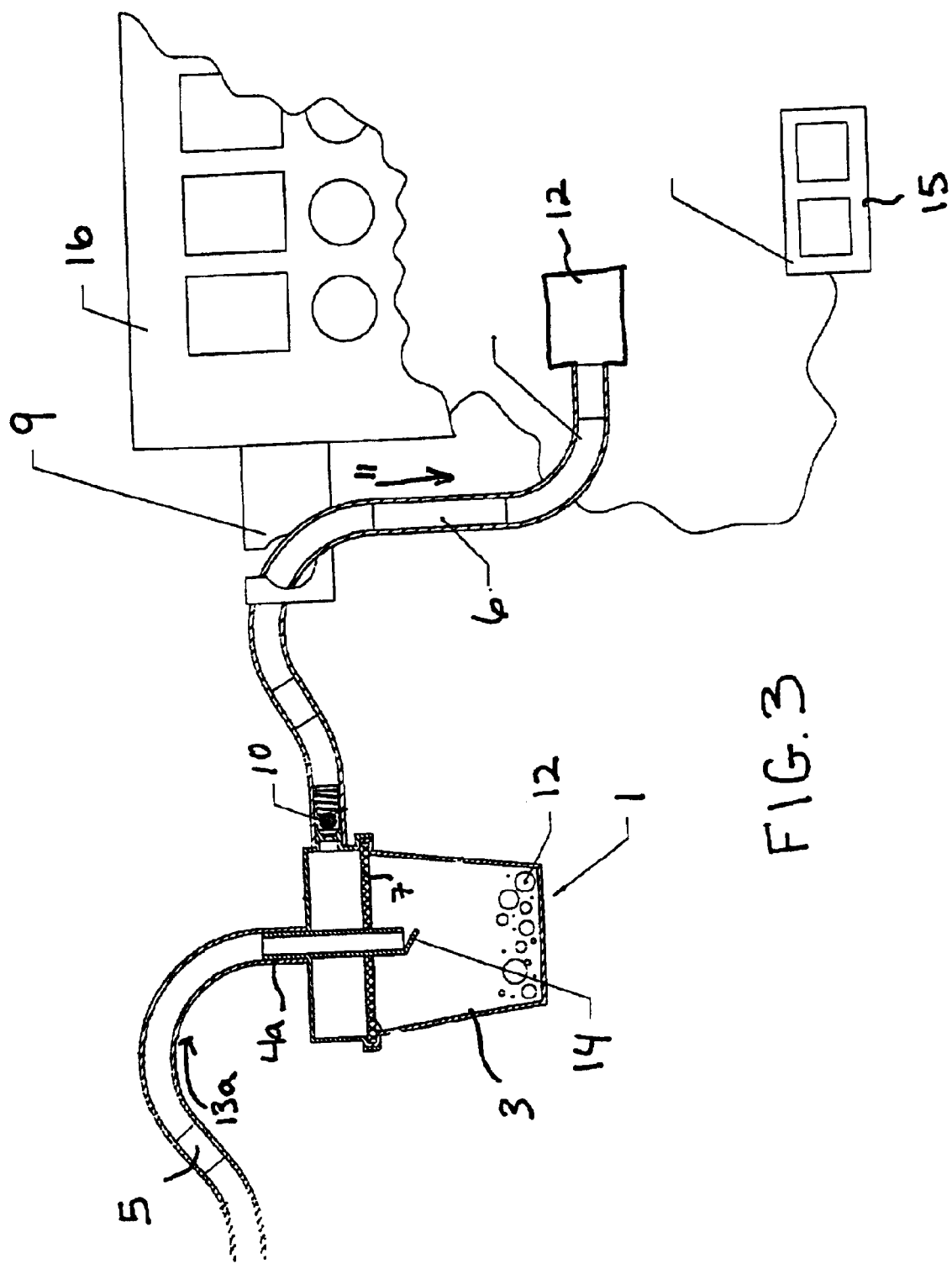

Collection zone 3 is designed in the form of a container 1a, and houses, in a fluid sealed fashion, functional zone 2, which in the example of FIGS. 1 to 3 has the form of a cover 1b which is screwed onto a threaded exterior surface of container 1a. Functional zone 2 is additionally provided with connecting elements 4a, 4b, one connecting element being intended for a supply suction line 5 and one connecting element being intended for a discharge suction line 6. A strainer or filter element 7 is disposed inside functional zone 2. Filter element 7 has a mesh size sufficient to screen out and separate the body materials from the body fluid. Filter 7 has a peripheral edge portion clamped between shoulders of container 1a and cover 1b, wherein filter 7 has a central aperture sealingly engaged around inlet conduit or supply suction line 5.

In FIG. 2, collection zone 3 illustrated according to FIG. 1 is shown in dot-dash outline, while functional zone 2 as illustrated in FIG. 1 has been replaced by a transportation cover The operation of the inventive filtration device is illustrated in FIG. 3. Filtration device 1 has a supply suction line 5 and a discharge suction line 6, discharge suction line 6 being routed through a peristaltic valve, preferably a pinch valve 9, to a suction pump 12. In addition, a lift check valve 10 is disposed upstream or downstream from pinch valve 9. Lift check valve 10 prevents a flow from acting counter to the direction of arrow 11.

Separated concrements 12 are sucked through supply suction line 5 together with liquid in the direction of the arrow 13 pointing toward filtration device 1, and they pass through connecting element 4a, whose free end projects into collection zone 3.

Concrements 12 are deposited by sedimentation. A strainer 7 prevents both liquid and concrements, fragments or the like from entering discharge suction line 6. In addition, a swing check valve 14 is disposed at the free end of connecting element 4a, at which supply suction line 5 is disposed. Thereby fragments are also prevented from moving back into the supply suction line against the actual suction stream 11.

When pinch valve 9 is released, as is illustrated in FIG. 3, the air is conveyed only toward suction pump 12. By simply unscrewing collection zone 3 and thus detaching it from functional zone 2, the extracted concrements, fragments or the like can be provided, without being transferred to a different vessel and filtered, with a transportation cover 8, so that this can also be labeled as an already complete transportation container, after which its contents can be examined by laboratory techniques or histologically.

The invention thus provides a means by which the fragments or other body material can be sucked under sterile conditions from body cavities in very simple manner, and can be delivered in very simple manner for laboratory or histological tests. Collection of this material for retention purposes is also possible hygienically.

A foot pedal 15 is provided, connected to control system 16 to control pinch valve 9 and suction pump 12.

Accordingly, while only a single embodiment of the present invention has been shown and described, it is to be understood that many changes and modifications may be made thereunto without departing from the spirit and scope of the invention as defined in the appended claims.

What is claimed is:

1. A filtration device for separating fragments and body material liquid in a body fluid comprising:
   a) a container having an upper open end, an inner peripheral upwardly facing axial shoulder adjacent said upper open end, and a threaded exterior surface adjacent said upper open end;
   b) a cover having an upper wall and a peripheral side wall defining a lower open end, an inner peripheral downwardly facing axial shoulder adjacent said lower open end, a threaded interior surface adjacent said downwardly facing shoulder threadedly engaged with the threaded exterior surface of said container, an outlet conduit extending through said peripheral sidewall of said cover, and an inlet conduit extending through the upper wall of said cover and into said container; and
   c) a filter having a peripheral edge portion clamped between the shoulders of the container and cover, said filter having a central aperture sealingly engaged around said inlet conduit;
   whereby body fluid flows downwardly through said inlet conduit into said container, liquid flows upwardly through said filter out of said discharge port while fragments and body material are retained in said container by said filter.

2. The filtration device according to claim 1, further comprising a check valve located within said outlet conduit.

3. The filtration device according to claim 1, further comprising a swing check valve disposed at an end of said inlet conduit and projecting into a collection zone located between a lower closed end of said container and said filter.

4. The filtration device according to claim 1, further comprising a transportation cover for mounting on said container to seal the contents thereof.

5. The filtration device according to claim 1, wherein said inlet and outlet conduits include flexible tubes connected thereto.

6. The filtration device according to claim 5, wherein said flexible tubes are disposable.

7. The filtration device according to claim 5, wherein said flexible tubes are plastic.

* * * * *